US008182756B2

(12) United States Patent
Liu et al.

(10) Patent No.: US 8,182,756 B2
(45) Date of Patent: May 22, 2012

(54) APPARATUS FOR PRODUCING AN INTERMEDIATE IN THE SYNTHESIS OF ACESULFAME POTASSIUM

(75) Inventors: Jicai Liu, Jiangsu (CN); Lingwen Kong, Jiangsu (CN); Zhongxiang Bao, Jiangsu (CN); Xiaoping Chen, Jiangsu (CN)

(73) Assignee: Suzhou Hope Technology Co., Ltd, Jiangsu (CN)

( * ) Notice: Subject to any disclaimer, the term of this patent is extended or adjusted under 35 U.S.C. 154(b) by 0 days.

(21) Appl. No.: 12/895,179

(22) Filed: Sep. 30, 2010

(65) Prior Publication Data

US 2011/0020191 A1 Jan. 27, 2011

Related U.S. Application Data

(62) Division of application No. 11/856,969, filed on Sep. 18, 2007, now Pat. No. 7,829,701.

(30) Foreign Application Priority Data

Sep. 24, 2006 (CN) .......................... 2006 1 0096179

(51) Int. Cl.
*B01J 19/00* (2006.01)
*C07D 291/00* (2006.01)

(52) U.S. Cl. ............................. 422/198; 422/129; 544/2

(58) Field of Classification Search .................. 422/129, 422/198; 544/2; 203/15
See application file for complete search history.

(56) References Cited

U.S. PATENT DOCUMENTS 3,427,342 A * 2/1969 Brooks et al. .................. 558/31
4,607,100 A 8/1986 Clauss et al.
4,876,341 A 10/1989 Schutz et al.
5,103,046 A 4/1992 Clauss et al.
5,744,010 A 4/1998 Roscher et al.
6,727,359 B2 4/2004 Tian et al.
2006/0193896 A1 8/2006 Boghani et al.

* cited by examiner

*Primary Examiner* — Walter D Griffin
*Assistant Examiner* — Natasha Young
(74) *Attorney, Agent, or Firm* — Myers Bigel Sibley & Sajovec, P.A.

(57) ABSTRACT

The invention discloses a kind of sulfonation cyclization technique for synthesizing acesulfame potassium for continuous production without stirring and special equipment for this technique. An injection pump is adopted to directly inject the sulfonation raw material and sulfonating agent into autoclave for sulfonation cyclization reaction under high velocity. Moreover, the reciprocating pump is adopted to deliver part of materials in autoclave to condenser designed outside the autoclave for cooling, followed by delivering the cooled materials to another input end of injection pump which together with sulfonation raw material and sulfonating agent is injected into autoclave through high-velocity injection by injection pump. The apparatus is composed of autoclave, injection pump, reciprocating pump and condenser.

12 Claims, 1 Drawing Sheet

1 2 3 4 5 6 8 9 7 10 11

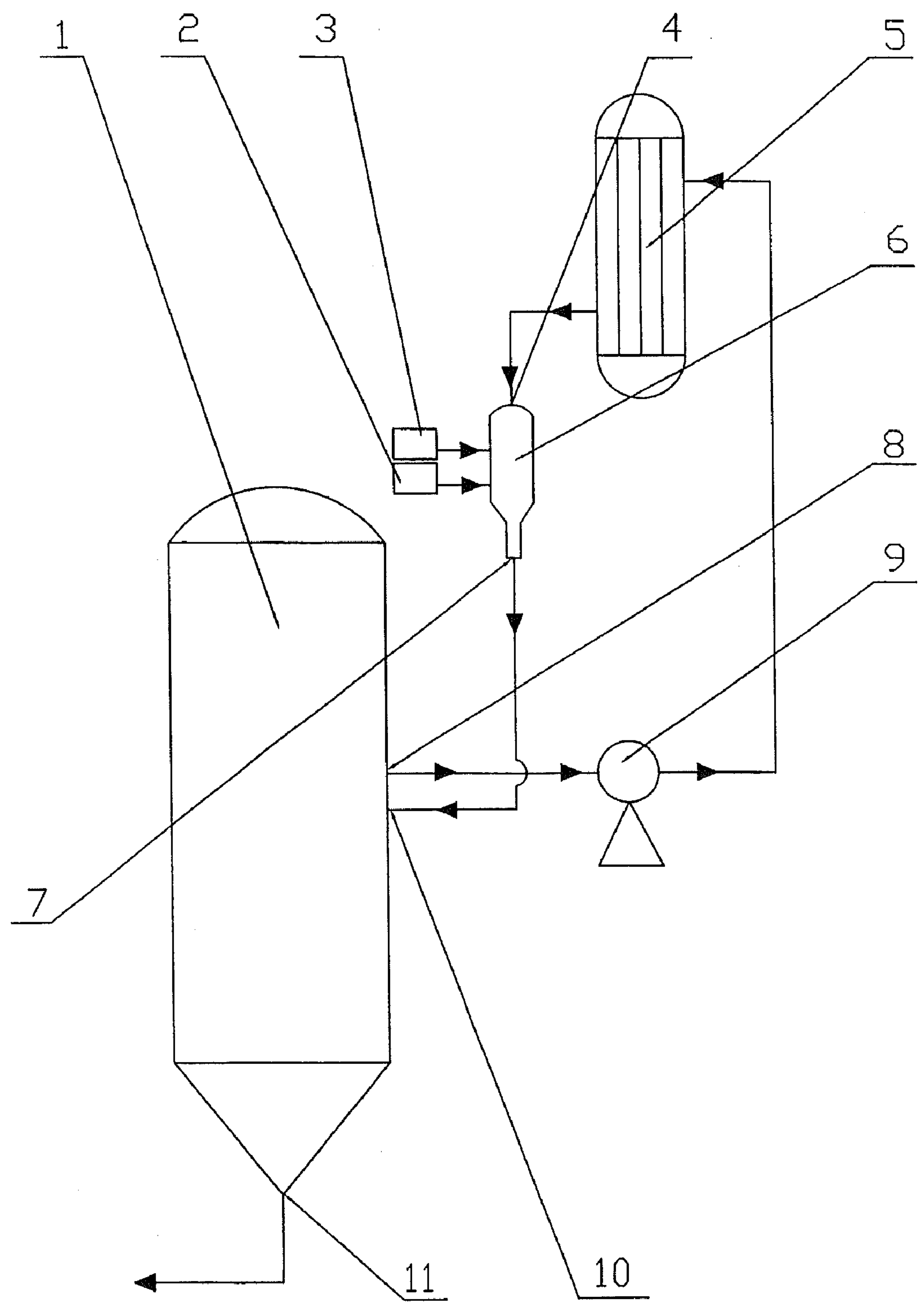
1
2
3
4
5
6
7
8
9
10
11

APPARATUS FOR PRODUCING AN INTERMEDIATE IN THE SYNTHESIS OF ACESULFAME POTASSIUM

CROSS-RELATED APPLICATIONS

This application is a divisional of U.S. patent application Ser. No. 11/856,969, now U.S. Pat. No. 7,829,701, filed Sep. 18, 2007, which claims priority from Chinese Patent Application No. 2006-10096179.0; filed Sep. 24, 2006, the disclosure of which is incorporated herein by reference in its entirety.

FIELD OF THE INVENTION

The present invention relates to a process for production of an intermediate for production of salts of 6-methyl-3,4-dihydro-1,2, 3-oxathiazin-4-one 2,2,-dioxide.

BACKGROUND OF THE INVENTION

Acesulfame potassium is one kind of sweetener widely used in foodstuff and beverage industry, which is characterized by good water solubility, high saccharinity, stable physicochemical property, strong synergized action and non-metabolism.

There are many ways to synthesize acesulfame potassium. A synthesis of acesulfame potassium is proposed in U.S. Pat. No. 4,695,629, wherein the reaction between raw material sulfamic acid and diketene is carried out by catalysis of triethylamine, followed by conducting sulfonation cyclization with sulfur trioxide and hydrolyzing to obtain acesulfame potassium. Other patents disclosing methods of synthesizing include U.S. Pat. Nos. 5,011,982 and 5,103,046. No special reaction equipment relating to sulfonation cyclization of sulfur trioxide and hydrolization has been found in other patents relating to synthesis of acesulfame potassium with sulfur trioxide as the sulfonating agent such as with respect to sulfonation cyclization reaction mentioned in these patents, generally, sulfonation raw material and sulfonating agent are added into autoclave for sulfonation cyclization reaction and the autoclave includes a stirring device to promote reaction. However, a cooling brine must be added into the jacket of autoclave during reaction to cool the heat discharged during reaction and control reaction temperature.

Research indicates that sulfur trioxide is a strong corrosive agent, oxidant, smoke substance and the adoption of common reaction equipment to carry out sulfonation cyclization reaction can easily result in leakage of sulfur trioxide, especially leakage easily occurs on the mechanical seal due to wear and tear by stirring. The leakage of sulfur trioxide may exert great negative impact on production and the environment since sulfur trioxide is a dangerous chemical product. In addition, only intermittent production can be conducted in terms of this type of reaction and the efficiency is low, while continuous production cannot be realized.

SUMMARY OF THE INVENTION

The present invention provides a process for continuous production of an intermediate used in the production of salts of 6-methyl-3, 4-dihydro-1,2,3-oxathiazin-4-one 2,2,-dioxide. The process comprises the first step of injecting a sulfonation raw material and a sulfonating reagent into a reactor, wherein said sulfonation raw material and sulfonating reagent are dissolved in an organic solvent to provide a reaction mixture of the sulfonation raw material and sulfonating reagent. Then a portion of the reaction mixture is removed from the reactor and cooled separate from the reaction mixture in the reactor. The cooled portion of the reaction mixture is combined back with the reaction mixture in that the reactor cyclization is allowed to occur to provide the desired intermediate in the synthesis of acesulfame potassium.

The present invention also provides an apparatus for the continuous production of the intermediate.

BRIEF DESCRIPTION OF THE DRAWINGS

The present invention now will be described more fully hereinafter with reference to the accompanying drawings, in which preferred embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. Like numbers refer to like elements throughout.

FIG. 1 illustrates an apparatus for production of the intermediate for sulfonation cyclization technique mentioned in the invention.

DETAILED DESCRIPTION OF THE EMBODIMENTS

Further descriptions on the invention disclosed herein will be made in the following on the basis of attached drawing and specific procedures.

Technical matters to be dealt with in the invention disclosed herein relates to a kind of sulfonation cyclization technique for synthesizing acesulfame potassium for continuous production without stirring and special equipment for the technique (e.g., liquid $SO_3$ or methylene chloride).

For the purpose of dealing with the above technical matters, the major technical principle elaborated in the invention is as follows: sulfonation raw material and sulfonating agent such as those detailed in U.S. Pat. Nos. 4,695,629 and 4,876,341, the disclosures of which are hereby incorporated by reference in their entireties, are injected into a reactor (e.g., an autoclave) through high-velocity injection by an injection pump to form a vortex to provide a reaction mixture. In one embodiment, the mol ratio of sulfonating agent to raw material is about 3 to 7 mol to 1 mol raw material, in another embodiment is 4 to 7 mol to 1 mol raw material, and in yet another embodiment is about 4 mol to 1 mol raw material. The raw material and sulfonating agent can be dissolved in an organic solvent such as, for example, a halogenated alkyl or alkene or an alkylene solvent (e.g., $CHCl_3$ or tetrachloride ethylene). A portion of the reaction mixture is removed and delivered, via a circulating pump, to a condenser for cooling. The cooled reaction mixture is returned to the reactor mixture and the remaining reaction mixture. In this manner, the need for a stirring device is eliminated and problems concerning leakage and intermittent production can be solved.

After the sulfonation cyclization reaction is complete, the resultant material (i.e., the desired intermediate) is discharged at the bottom of autoclave, and is then used to synthesize salts of 6-methyl-3,4-dihydro-1,2, 3-oxathiazin-4-one 2,2,-dioxide.

The temperature of aforesaid material which has been cooled in condenser can be preferably controlled at −50° C. to about −15° C., and in one embodiment is controlled at about −45° C. to about −20° C.

The apparatus used in sulfonation cyclization technique includes autoclave, feed opening and feed back hole designed on the side wall of autoclave with the feed opening locating below feed back hole, discharge hole at the bottom of autoclave, and feed opening connected to the outlet of injection pump, and feed back hole connected to the inlet of reciprocating pump, and the outlet of reciprocating pump connected to the inlet of condenser, and the outlet of condenser connected to one input end of injection pump and two input ends of injection pump separately connected to sulfonation raw material and sulfonating agent.

As indicated in FIG. 1, the apparatus for the aforesaid sulfonation cyclization technique includes autoclave 1, feed opening 10 and feed back hole 8 designed on the side wall of autoclave 1 with the feed opening 10 locating below feed back hole 8, discharge hole 11 at the bottom of autoclave 1, and feed opening 10 connected to the outlet 7 of injection pump 6, and feed back hole 8 connected to the inlet of reciprocating pump 9, and the outlet of reciprocating pump 9 connected to the inlet of condenser 5, and the outlet of condenser 5 connected to one input end 4 of injection pump 6 and two input ends of injection pump 6 separately connected to sulfonation raw material 2 and sulfonating agent 3.

Sulfonation cyclization technique mentioned in the invention disclosed herein with adoption of the aforesaid apparatus is detailed as follows: the sulfonation raw material 2 and sulfonating agent 3 are separately delivered into two input ends of injection pump 6, which are directly injected into autoclave 1 for sulfonation cyclization reaction by injection pump 6; meanwhile, reciprocating pump 9 is adopted to deliver a portion of the reaction mixture in autoclave 1 to condenser 5 for cooling, with temperature of material which has been cooled in condenser 5 being controlled at −50° C. to about −15° C., followed by delivering the cooled reaction mixture to another input end 4 of injection pump 6 which together with sulfonation raw material 2 and sulfonating agent 3 is injected into autoclave 1 through high-velocity injection by injection pump 6. After the sulfonation cyclization reaction, the resultant materials are discharged through discharge hole 11 at the bottom of autoclave 1.

Based on the above, negative pressure generated during high-velocity injection by injection pump 6 is more conducive to injecting sulfonation raw material 2, sulfonating agent 3 and materials cooled in condenser 5 into autoclave 1 to form a vortex on the inside wall of autoclave 1, thus allowing the complete sulfonation cyclization reaction to occur without stirring. Moreover, removing a portion of the reaction mixture for cooling outside the autoclave 1 can better control the temperature of reactants; therefore, sulfonation cyclization technique and apparatus for the technique mentioned in the invention disclosed herein can bring about continuous production and greatly improve productivity.

That which is claimed is:

1. An apparatus for carrying out sulfonation cyclization that reduces the leakage of sulfonating reagent during continuous production of the salts of 6-methyl-3,4-dihydro-1,2,3-oxathiazin-4-one 2,2,-dioxide comprising:

(a) a reactor to carry out a sulfonation cyclization reaction, (b) a high-velocity injection pump to introduce a mixture of sulfonation raw material and sulfonating reagent into the reactor through high-velocity injection to provide a reaction mixture and to form a vortex of the reaction mixture in the reactor, (c) a reciprocating pump to remove a portion of the reaction mixture, and (d) a means for cooling the portion of the reaction mixture removed from the reactor.

2. The apparatus of claim 1, wherein the cooled portion of the reaction mixture is delivered to the high-velocity injection pump and the high-velocity injection pump injects a mixture of the sulfonation raw material, the sufonating reagent and the cooled portion of the reaction mixture into the reactor, wherein high-velocity injection of the mixture of the sulfonation raw material, the sufonating reagent and the cooled portion of the reaction mixture into the reactor maintains the vortex of the reaction mixture remaining in the reactor so as to avoid the need for stirring to continue continuous production of salts of 6-methyl-3,4-dihydro-1,2,3-oxathiazin-4-one 2,2-dioxide by sulfonation cyclization.

3. The apparatus of claim 1, wherein the reactor comprises a feed inlet and a feed outlet on the sidewall of the reactor, and a discharge outlet at the bottom of the reactor.

4. The apparatus of claim 3, wherein the feed inlet of the reactor is connected to the outlet of the high-velocity injection pump, the feed outlet of the reactor is connected to the inlet of the reciprocating pump, the outlet of the reciprocating pump is connected to the inlet of the means for cooling and the outlet of the means for cooling is connected to at least one inlet of the high-velocity injection pump.

5. The apparatus of claim 1, wherein the means for cooling and the injection pump are positioned above the reactor and the reciprocating pump.

6. The apparatus of claim 1, wherein said reactor is an autoclave.

7. The apparatus of claim 1, wherein the portion of the reaction mixture removed from the reactor is cooled to about −50° C. to about −15° C.

8. The apparatus of claim 1, wherein the portion of the reaction mixture removed from the reactor is cooled to about −45° C. to about −20° C.

9. The apparatus of claim 1, wherein the sulfonating reagent is liquid $SO_3$.

10. The apparatus of claim 1, wherein the mixture of sulfonation raw material and sulfonating reagent is dissolved in an organic solvent.

11. The apparatus of claim 10, wherein the organic solvent is a halogenated alkyl, alkene or alkylene.

12. The apparatus of claim 11, wherein the organic solvent is selected from the group consisting of $CH_2Cl_2$, $CHCl_3$ and tetrachloroethene ($Cl_2C{=}CCl_2$).

* * * * *